(12) United States Patent
Sheltraw et al.

(10) Patent No.: US 8,934,691 B2
(45) Date of Patent: Jan. 13, 2015

(54) SYSTEM FOR MOTION COMPENSATED MR PARALLEL IMAGING

(75) Inventors: Daniel James Sheltraw, Albany, CA (US); Vibhas S. Despande, Sunnyvale, CA (US); Benjamin Alastair Inglis, Lafayette, CA (US)

(73) Assignees: Siemens Medical Solutions USA, Inc., Malvern, PA (US); The Regents of the University of California, Oakland, CA (US)

( * ) Notice: Subject to any disclaimer, the term of this patent is extended or adjusted under 35 U.S.C. 154(b) by 403 days.

(21) Appl. No.: 13/412,766

(22) Filed: Mar. 6, 2012

(65) Prior Publication Data

US 2012/0257806 A1 Oct. 11, 2012

Related U.S. Application Data

(60) Provisional application No. 61/472,328, filed on Apr. 6, 2011.

(51) Int. Cl.
*G06T 9/00* (2006.01)
*G06T 5/00* (2006.01)
(Continued)

(52) U.S. Cl.
CPC .................. *A61B 5/721* (2013.01); *A61B 5/055* (2013.01); *G01R 33/56509* (2013.01); *G01R 33/482* (2013.01); *G01R 33/5611* (2013.01); *G01R 33/5616* (2013.01); *A61B 2560/0223* (2013.01)
USPC ........... 382/131; 382/128; 382/132; 382/254; 382/275; 382/280

(58) Field of Classification Search
CPC ..... G06T 5/003; G06T 7/0012; G06T 7/0016; G06T 7/20; G06T 7/206; G06T 2207/10088; G06T 2207/20201; A61B 5/05; A61B 5/0515; A61B 5/0522; A61B 6/03; A61B 6/4007; A61B 6/4014; A61B 6/5258; A61B 6/5264
USPC .................. 382/131, 128, 132, 254, 275, 280
See application file for complete search history.

(56) References Cited

U.S. PATENT DOCUMENTS 5,553,157 A * 9/1996 Bourguignon et al. ....... 382/131
6,341,179 B1   1/2002 Stoyle et al.
(Continued)

OTHER PUBLICATIONS

Lin, et al. "Motion Correction Using an Enhanced Floating Navigator and GRAPPA Operations." Magnetic Resonance in Medicine. 63. (2010): 339-348. Print.*
(Continued)

*Primary Examiner* — Michael A Newman
(74) *Attorney, Agent, or Firm* — Peter R. Withstandley (57) ABSTRACT

An MR system compensates for patient movement by generating a magnetic field for acquiring, first data representing individual frequency components of a segment of a k-space storage array during a first time period and second data representing individual frequency components of the segment of the k-space storage array during a subsequent second time period. The first and second data comprise individual frequency components of different images of a portion of the anatomy of a patient. The system uses the first and second data in calculating a measure representing degree of patient related motion occurring between acquisition of the first data and second data and generates an image by excluding frequency components of the first data and second data in response to the calculated measure exceeding the predetermined threshold value.

14 Claims, 7 Drawing Sheets

(51) Int. Cl.
  *A61B 5/05*   (2006.01)
  *A61B 5/00*   (2006.01)
  *A61B 5/055*  (2006.01)
  *G01R 33/565* (2006.01)
  *G01R 33/48*  (2006.01)
  *G01R 33/561* (2006.01)

(56) References Cited

U.S. PATENT DOCUMENTS

| | | | |
|---|---|---|---|
| 6,777,933 B2 | 8/2004 | Stoyle | |
| 6,850,061 B2 | 2/2005 | Stoyle | |
| 6,900,631 B2* | 5/2005 | Bydder et al. | 324/307 |
| 7,102,348 B2* | 9/2006 | Zhang et al. | 324/309 |
| 7,308,125 B2 | 12/2007 | Atkinson | |
| 8,073,522 B2 | 12/2011 | Stemmer | |
| 8,155,389 B2* | 4/2012 | Parker et al. | 382/107 |
| 8,330,461 B2* | 12/2012 | Madore | 324/309 |
| 8,649,579 B2* | 2/2014 | Griswold et al. | 382/128 |
| 8,653,816 B2* | 2/2014 | Lake et al. | 324/309 |
| 2003/0130574 A1 | 7/2003 | Stoyle | |
| 2004/0114791 A1 | 6/2004 | Atkinson | |
| 2007/0205769 A1* | 9/2007 | Yui et al. | 324/318 |
| 2009/0087057 A1* | 4/2009 | Parker et al. | 382/131 |

OTHER PUBLICATIONS

Kadah, Yasse. "Motion Artifact Suppression in MRI using k-Space overlap processing." 25th National Radio Science Conference. (2008): 1-9. Print.*

Samsonov, et al. "POCS-Enhanced Correction of Motion Artifacts in Parallel MRI." Magn Rson Med. 63.4 (2010): 1104-1110. Print.*

Mark A Griswold, et al., "Generalized Autocalibrating Partially Parallel Acquisitions (GRAPPA)", Magnetic Resonance in Medicine 47:1202-1210 (2002).

Anja C.S. Brau, et al, "Comparision of Reconstruction Accuracy and Efficiency Among Autocalibrating Data-Driven Parallel Imaging Methods", Magnetic Resonance in Medicine 59:382-395 (2008).

Felix A Breuer, et al., "Dynamic Autocalibrated Parallel Imaging Using Temporal GRAPPA (TGRAPPA)", Magnetic Resonance in Medicine 47:1202-1210 (2002).

Richard L. Ehman, Joel P. Felmlee, "Adaptive Technique for High-Definition MR Imaging of Moving Structures", Radiology, 1989; 173:255-263.

D. Sheltraw, V. Deshpande, M. Trumpis and B. Inglis, "Simultaneous Reduction of Two Common Autocalibration Errors in GRAPPA EPI Time Series Data", submitted to Neuroimage on Jan. 25, 2012.

* cited by examiner

FIGURE 1

Prior Art

SYSTEM FOR MOTION COMPENSATED MR PARALLEL IMAGING

CROSS-REFERENCE TO RELATED APPLICATIONS

This application is a non-provisional of, and claims priority to, U.S. provisional patent application Ser. No. 61/472,328 filed on 6 Apr. 2011, incorporated herein by reference in its entirety.

FIELD OF THE INVENTION

This invention concerns a system for compensating for patient movement related artifacts occurring in MR imaging by generating an image using acquired individual frequency components of adjacent segments of a k-space storage array excluding frequency components of different images of a single image slice in response to a calculated measure representing degree of patient related motion occurring between the different images.

BACKGROUND OF THE INVENTION

Parallel MRI increases image acquisition speed by using spatial sensitivity of an array of receiver coils in addition to the spatial encoding provided by applied linear magnetic field gradients. The additional spatial information enables reduction in the number of acquired phase-encoding (PE) k-space lines needed for conventional image reconstruction and therefore accelerates data acquisition. The increase in image acquisition speed is usually stated in terms of the reduction factor R which, for fixed nominal image resolution and field-of-view (FOV), comprises the ratio of the number of acquired PE lines for a conventional scan to the number of acquired PE lines for a parallel imaging scan. The PE lines which are absent from the parallel imaging data set are termed herein the missing set and the data sampled during accelerated imaging is termed herein the reduced set of PE lines. In addition the union of the reduced set and the missing set are referred to as the nominal set of PE lines which are equivalent to the set of PE lines acquired during conventional imaging since it is the sampling characteristics of this set which determines the nominal digital image resolution and FOV.

Known GRAPPA (GeneRalized Autocalibrating Partially Parallel Acquisitions) parallel imaging does not require explicit knowledge of receive fields for each element of a receiver array. Instead, the GRAPPA method uses data from the receiver array in an auto-calibration procedure which determines a set of synthesis coefficients used to synthesize the missing set of PE lines from the reduced set of PE lines over the set of receiver coils. The autocalibration procedure acquires a set of auto-calibration scan (ACS) lines which are a subset of the nominal PE lines. It is these ACS lines which are used to calculate synthesis coefficients over a set of receiver array channels.

Figure 1:
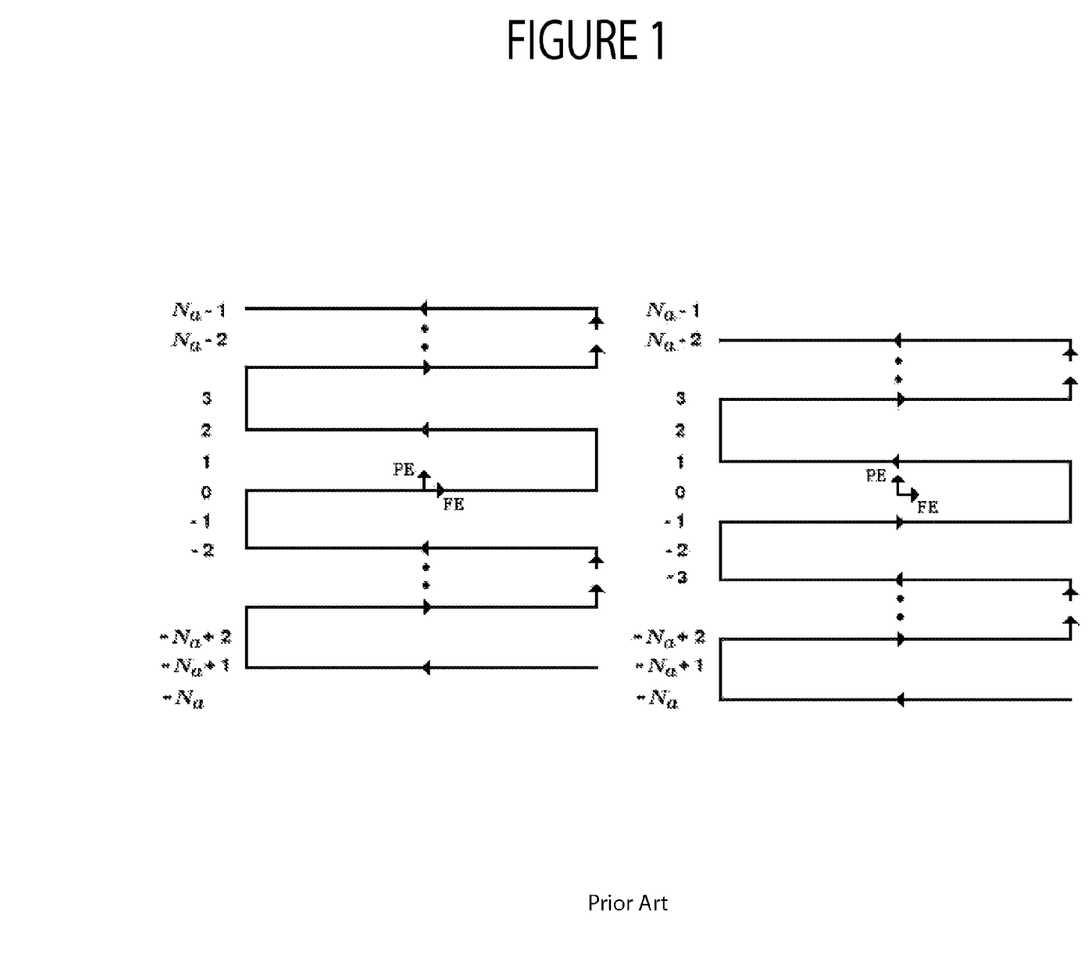
FIG. 1 shows two segments of an interleaved ACS k-space trajectory for R=2 with phase encoding direction being vertical and the frequency-encoding direction being horizontal.

For a GRAPPA EPI (echo planar imaging) time series, the ACS data is often collected on k-space trajectories which sample the data in a segmented interleaved fashion, as depicted in FIG. 1 for R=2. FIG. 1 shows two segments of a 2-shot interleaved ACS k-space trajectory having a vertical phase-encoding direction and a horizontal frequency-encoding direction. In FIG. 1 the total number of ACS lines $N_a$ is not necessarily equal to the nominal matrix size in the PE direction. Further, interleaved EPI ACS is sensitive to motion corruption. If motion (e.g., due to respiration, heart rate or patient movement, for example) occurs between the sampling of the interleaved ACS segments, artifacts, most notably residual aliasing, occur in GRAPPA-reconstructed EPI images. A system according to the present invention addresses this deficiency and related problems.

SUMMARY OF THE INVENTION

A system for parallel MR imaging according to an embodiment of the present invention uses an auto-calibration scan (ACS) to partially and indirectly determine the receive fields of each element of an array of receiver coils. The system compensates for patient movement related artifacts occurring in MR imaging. In one non-limiting embodiment, the system comprises a magnetic field generator and an image data processor. The magnetic field generator generates a magnetic field for use in acquiring, first data representing individual frequency components of a segment of a k-space storage array during a first time period and second data representing individual frequency components of the segment of the k-space storage array during a second time period subsequent to the first time period. The first data and the second data comprise individual frequency components of different images of a portion of the anatomy of a patient. The image data processor uses the first data and second data in calculating a measure representing degree of patient related motion occurring between acquisition of the first data and second data. The image data processor compares the calculated measure with a predetermined threshold value and generates an image using acquired individual frequency components of adjacent segments of the k-space storage array excluding frequency components of the first data and second data in response to the calculated measure exceeding the predetermined threshold value.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

In accordance with an embodiment of the present invention, a system for parallel MR imaging uses an auto-calibration scan (ACS) to partially and indirectly determine the receive fields of each element of an array of receiver coils. For EPI time series, the ACS data is acquired along various k-space trajectories. In this setting the interleaved R-shot EPI trajectory, where R is the GRAPPA reduction factor, offers advantages. Unfortunately, interleaved R-shot EPI ACS can suffer due to motion occurring between the shots of the interleaved ACS and this motion may lead to artifacts in GRAPPA-reconstructed images. Accordingly, our inventive system acquires and assesses interleaved ACS data in a manner which preserves the advantages of R-shot interleaved EPI ACS data acquisition while also mitigating the effects of motion between the R ACS shots. In one embodiment the system makes use of the phase correction data, conveniently a part of many standard EPI sequences, to assess the motion between the segments of R-shot EPI ACS scans. The phase correction scans serve as navigator echoes to which a root-mean-square deviation motion metric is applied for the determination of the best available complete ACS dataset among multiple complete sets of ACS data. This best set is used in a GRAPPA auto-calibration algorithm.

The system reduces motion corruption of segmented EPI GRAPPA Auto-Calibration Data and acquires R-shot interleaved EPI ACS data and minimizes the effects of motion. The system employs multiple R-shot interleaved ACS EPI data sets and phase correction data, which is part of most existing EPI sequences, to assess motion between ACS EPI segments and produce a complete set of ACS EPI data which is not corrupted by motion. The complete set of ACS segments is used to calculate GRAPPA synthesis coefficients and to synthesize the missing PE lines.

Figure 2:
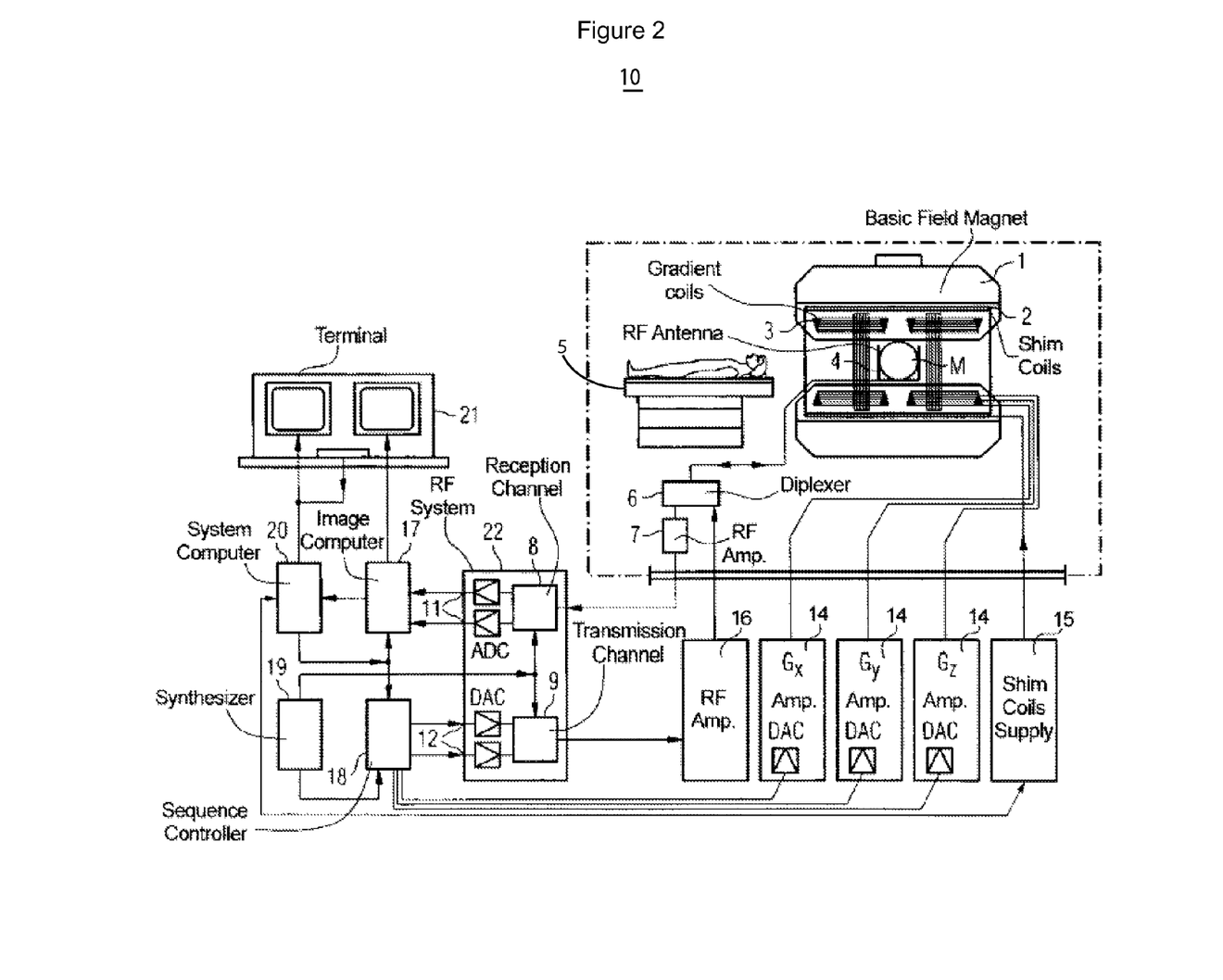
FIG. 2 shows an MR imaging unit including a system for compensating for patient movement related artifacts occurring in MR imaging, according to an embodiment of the invention.

FIG. 2 shows an MR imaging unit 10 including a system for compensating for patient Movement related artifacts occurring in MR imaging according to an embodiment of the invention. RF coils 4 emit RF pulses to excite nuclear proton spins in a patient on support table 5 in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

MR imaging unit 10 also includes a system for compensating for patient movement related artifacts occurring in MR imaging. A magnetic field generator (RF coils 4) generates a magnetic field for use in acquiring, first data representing individual frequency components of a segment of a k-space storage array during a first time period and second data representing individual frequency components of the segment of the k-space storage array during a second time period subsequent to the first time period. The first data and the second data comprise individual frequency components of different images of a portion of the anatomy of a patient. An image data processor (not shown to preserve drawing clarity) in system computer 20, uses the first data and second data in calculating a measure representing degree of patient related motion occurring between acquisition of the first data and second data. The image data processor compares the calculated measure with a predetermined threshold value and generates an image using acquired individual frequency components of adjacent segments of the k-space storage array excluding frequency components of the first data and second data in response to the calculated measure exceeding the predetermined threshold value.

In the 2D multislice GRAPPA method the missing phase-encoding (PE) lines are synthesized according to the following equation, $$S_n(k_x, k_y + r\Delta k_y) = \sum_{j=1}^{N_c} \sum_{\tau_y}^{d_y} W_{njr}(\tau_y) S_j(k_x, k_y + \tau_y R \Delta k_y) \quad [1]$$

where $S_n(k_x,k_y)$ is the signal in the $n^{th}$ receiver coil at k-space coordinates $(k_x,k_y)$, R is the reduction factor, r=1, ..., R−1 is the PE offset from an ACS PE line to a missing PE line, $\Delta k_y$ is the distance from one phase-encode line to the next in a complete ACS data set, $N_c$ is the number of coil elements in the receiver array, dy is the number of PE points used in a local interpolating block, and $W_{njr}(\tau y)$ comprises the synthesis coefficients. Equation 1 is used in conjunction with the sampled ACS lines to perform an auto-calibration step to obtain synthesis coefficients using a fitting algorithm.

In response to determining the coefficients $W_{njr}(\tau y)$, Equation 1 is used to synthesize the missing set of PE lines from the reduced set of PE lines for individual receiver coils. The images from each coil are reconstructed by performing an FFT (Fast Fourier Transform) of the complete set of PE lines followed by a square-root of a sum-of-squares combination of data of individual coil images to produce a resultant image. For a time series of EPI data, the methods of ACS acquisition may be separated into two classes: (1) A non-embedded method in which a complete set of ACS data is acquired once prior to the acquisition of the time series data and, (2) An embedded method in which complete sets of ACS lines are acquired repeatedly throughout an EPI time series. In the non-embedded class the number of ACS lines Na (see FIG. 1) is usually significantly smaller than the nominal size $N_s$ the sampling matrix in the PE direction. In this case a single calculation of the synthesis coefficients is done followed by repeated calculations of the missing PE lines from the reduced data sets at each discrete time point n of the time series. In the embedded class the time series is comprised of a sequential and repeated sampling of R interleaves of EPI data. For example, if R=2, reduced data sets at sequential time points n and n+1 in the time-series are respectively sampled over first and second trajectories given in FIG. 1. In this case $N_a=N_s$ since there is no distinction between the ACS data and the reduced data set. However, a subset of the $N_s$ PE lines acquired during R interleaves may be used to calculate the synthesis coefficients at each timepoint n in the time series: The synthesis coefficients corresponding to a time point n are used to synthesize the missing data from the reduced data set acquired at time point n. Embedded and non-embedded ACS scans are both susceptible to motion occurring between the interleaves of ACS EPI segments.

Figure 3:
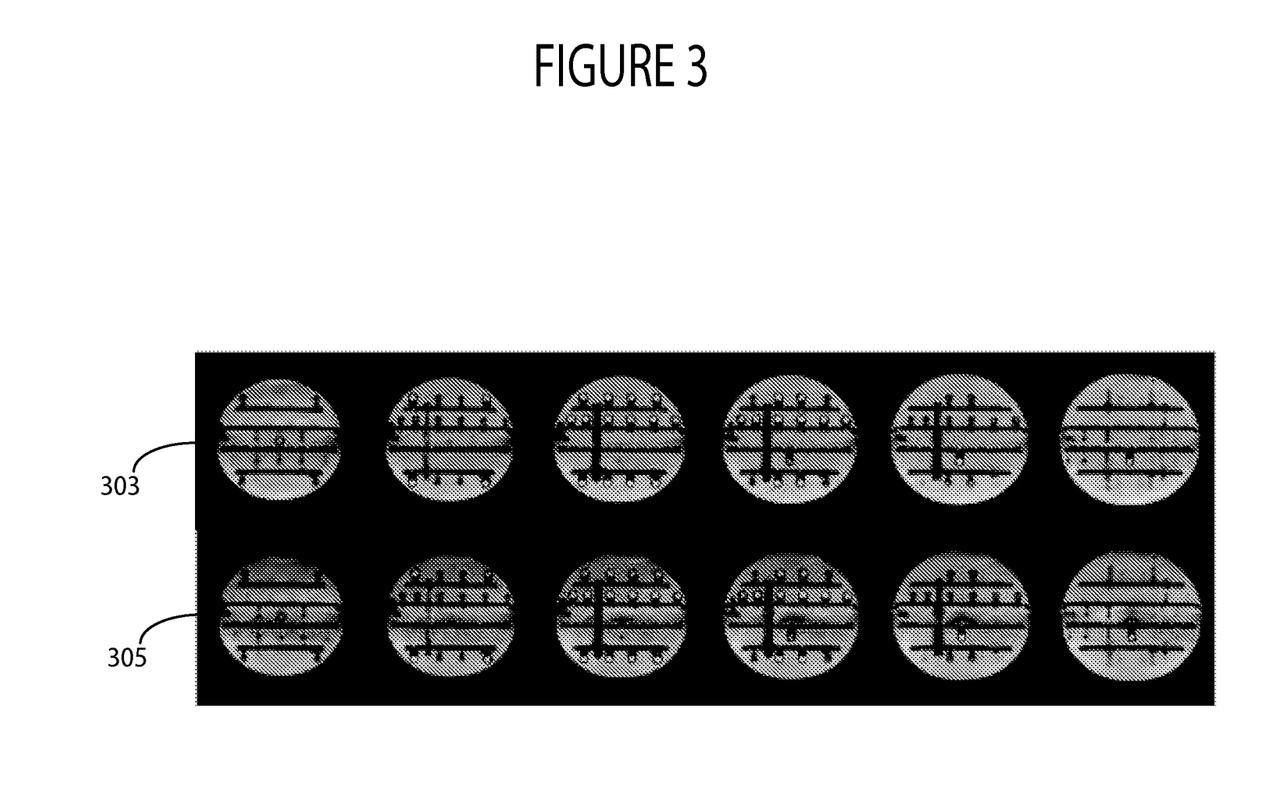
FIG. 3 shows successive images slices (top row) acquired using GRAPPA with R=3 reconstructed using a 3-shot interleaved ACS data acquisition according to an embodiment of the invention, and a corresponding set of image slices (bottom row) acquired using GRAPPA with R=3 using a single-shot ACS data acquisition.

For a non-embedded ACS method, a motion artifact may potentially be eliminated by using a 1-shot rather than an R-shot interleaved EPI k-space trajectory. However, the R-shot trajectory has the advantage of eliminating residual aliasing that may occur when the signal dynamics over a 1-shot ACS sampling trajectory differ significantly from that over the reduced data set trajectory, as may occur in the presence of main field inhomogeneity. FIG. 3 shows, for the case of R=3, an example of the aliasing that may result when 1-shot ACS data is used to autocalibrate the synthesis coefficients. Such artifacts are to be expected since the $W_{njr}(\tau y)$ depends upon spatial encoding functions which map between image-space and k-space. In the presence of significant main field inhomogeneity the encoding functions are modified in a manner which depends upon the k-space sampling trajectory used in the autocalibration.

FIG. 3 shows successive images slices (top row 303) acquired using GRAPPA with R=3 reconstructed using a 3-shot interleaved ACS data acquisition and a corresponding set of image slices (bottom row 305) acquired using GRAPPA with R=3 using a single-shot ACS data acquisition. Residual aliasing extends throughout the images of row 305. Exterior to the phantom, the residual aliasing appears as misplaced image intensity while interior to the phantom the residual aliasing appears as both increased and decreased local image intensity.

Figure 4:
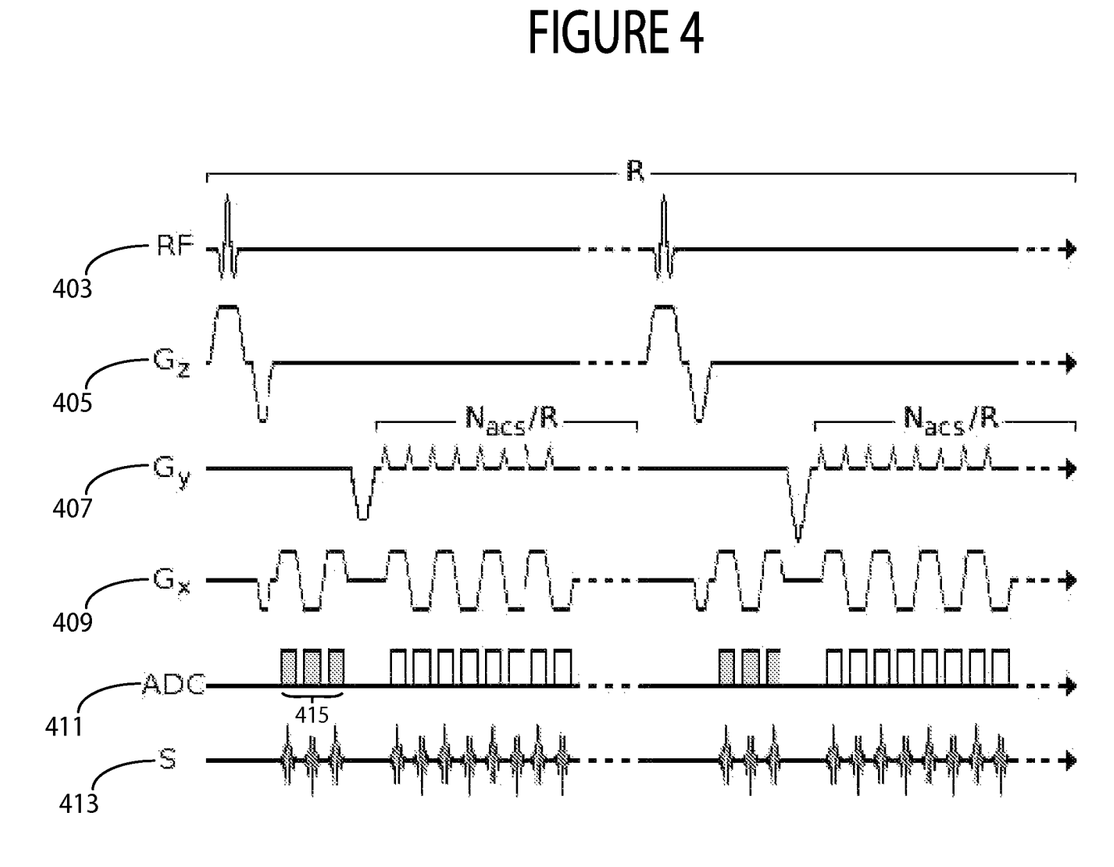
FIG. 4 shows a pulse sequence diagram used for the acquisition of a complete set of ACS data, according to an embodiment of the invention.

FIG. 4 shows a pulse sequence diagram used for the acquisition of a complete set of ACS data. $G_x$ 409, $G_y$ 407 and $G_z$ 405 denote the frequency-encoding, in-plane phase-encoding and through-plane phase-encoding gradients respectively. The gray filled analog-to-digital converter (ADC) regions 415 of ADC signal 411 identifies the phase correction data lines which are also used as navigator echoes to detect motion between interleaved ACS segments. The prephasing $G_y$ 407 gradient is incremented for each ACS segment to achieve interleaving. RF excitation signal 403 and signal intensity S 413 are also shown.

The inventive system substantially eliminates residual aliasing due to motion between ACS segments. The phase correction lines 415 which precede each 2D slice in commercial EPI sequences are used as navigator echoes to assess whether motion has occurred between the segments of a complete ACS data set. The R adjacent segments that have the least associated motion, according to a motion metric, are used in a calculation of synthesis coefficients thereby effectively eliminating motion-related residual aliasing. In one embodiment, a metric $M_s$ for assessing motion between R segments of the $s^{th}$ complete ACS data set is a normalized root-mean-square deviation, $$M_s = \sqrt{\frac{\sum_{m=1}^{N_c}\sum_{n=1}^{N_s}\sum_{j=1}^{R-1}\|S_{sjm}[n]-S_{s,j+1,m}[n]\|^2}{\sum_{m=1}^{N_c}\sum_{n=1}^{N_s}\|S_{s1m}[n]\|^2}} \quad [2]$$

where $S_{sjm}[n]$ is the frequency-encoded signal (which may be an FFT of the raw signal, for example), j is the ACS segment index, m is the coil element index and n is the signal sample index. Complete ACS data sets with smaller associated $M_s$ advantageously produce EPI images with less residual aliasing.

In an example of operation, multi-slice 2D images are acquired on a Siemens TIM Trio 3T whole-body scanner with a 12-channel phased array head receiver coil using GRAPPA with R=2, echo-spacing time of 0.8 ms, nominal matrix size of 64×64 ($N_s \times N_s$), and a TR of 2000 ms. A standard EPI sequence is modified to acquire 10 complete ACS data sets instead of a usual single complete set. Each interleaved ACS EPI segment acquired 12 PE lines for a total of 24 ACS lines ($N_a=24$) in a complete ACS data set. Following the ACS acquisition a single volume of 2D multi-slice image data (a reduced set) is acquired. Four separate data trials are acquired. During the acquisition of the first three data trials the subject nodded his head in randomly distributed 4-second intervals between which the subject tried to remain motionless. During the acquisition of the fourth data trial the subject tried to remain motionless throughout the acquisition of the 10 complete ACS datasets.

The modified EPI sequence acquires three phase correction lines prior to each 2D slice of image data. Using Equation 2, $M_s$ associated with each phase correction line is calculated and the system averages the three Ms values to yield the final $M_s$ value for each of the 10 complete ACS data sets of a given trial. From each complete ACS data set the synthesis coefficients are calculated using a GRAPPA method. The missing set of PE lines is reconstructed using the reduced data set of PE lines and the synthesis coefficients corresponding to each of the 10 complete ACS sets. This is done for each of the twelve coil elements, after which the data is Fourier transformed to image-space and the images from each coil are combined in a final sum-of-squares image.

Figure 5:
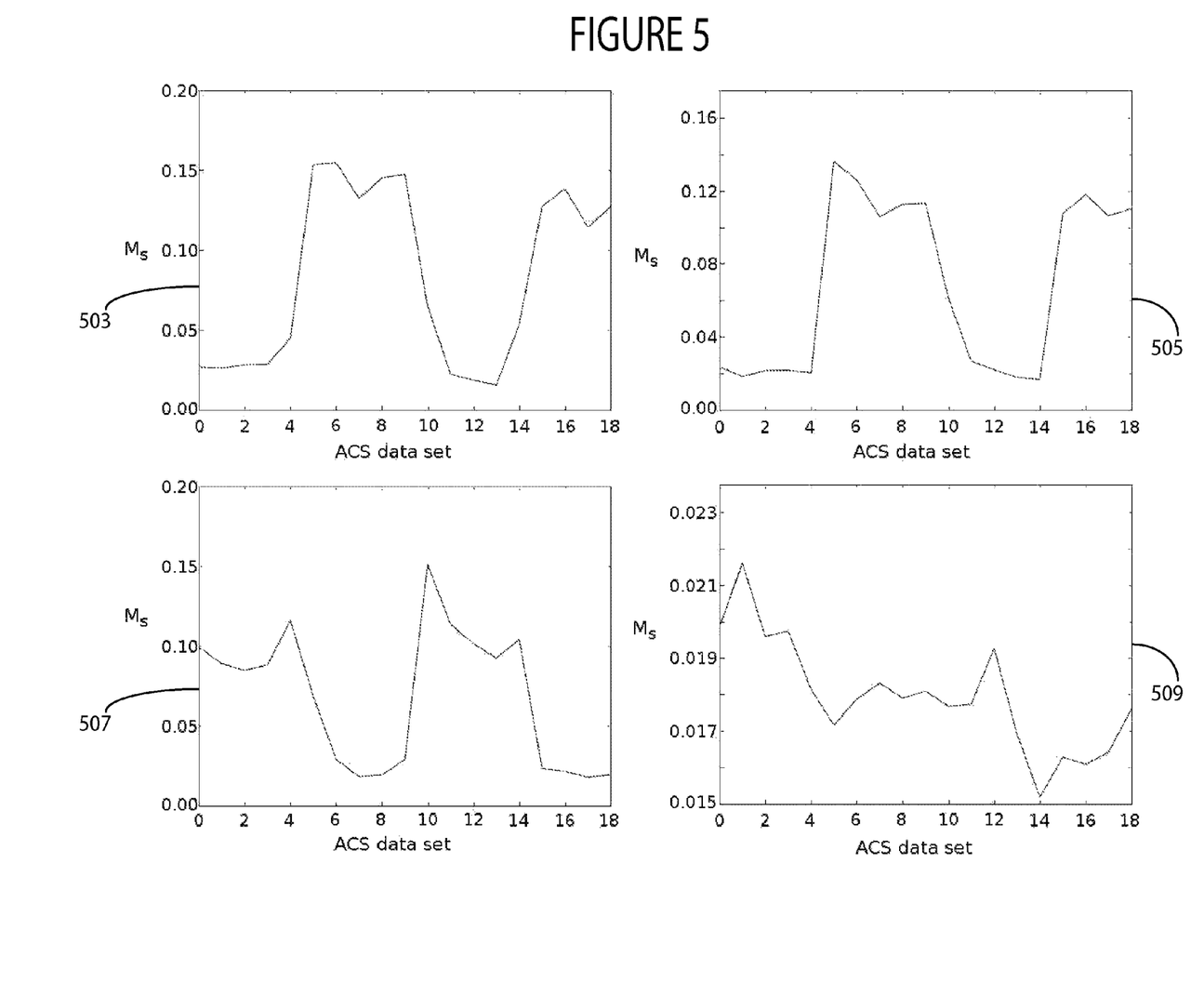
FIG. 5 shows graphical plots of a motion metric as a function of the $n^{th}$ complete ACS data set, according to an embodiment of the invention.
Figure 6:
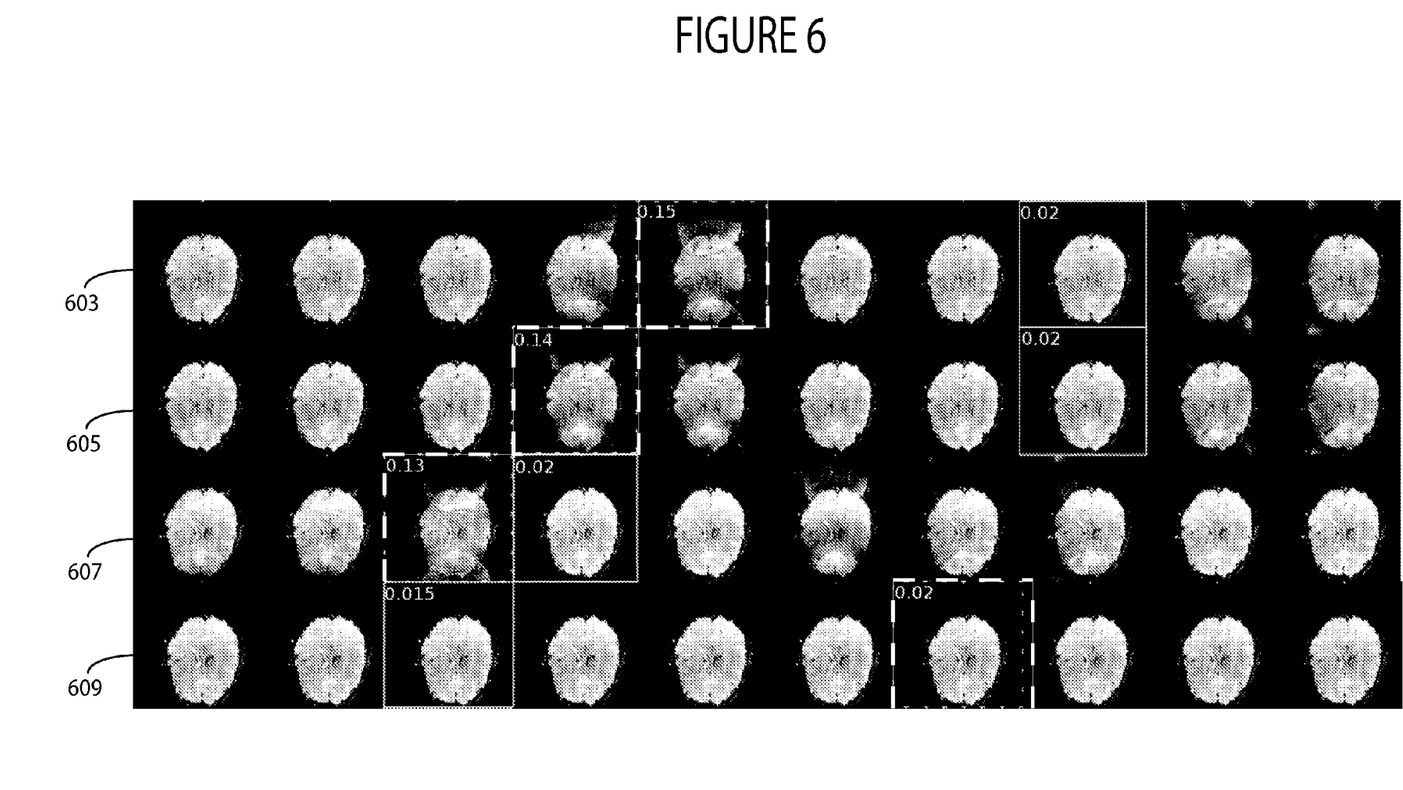
FIG. 6 shows images reconstructed from ACS data sets during which subject motion was introduced, according to an embodiment of the invention.

FIGS. 5 and 6 show the results for an EPI GRAPPA R=2 acquisition. The 20 adjacent pairs of acquired interleaved ACS segments can be grouped in 19 complete ACS data sets, using next nearest pairs and to reduce magnetic field drift effects. FIG. 5 shows plots of the motion metric $M_s$ associated with each of the 19 complete ACS data sets as a function of the $n^{th}$ complete ACS data set. Plots 503, 505, 507 and 509 correspond respectively to image sequence rows 603, 605, 607 and 609 of FIG. 6. The scale of the y-axis ordinate varies between the four plots.

FIG. 6 shows the EPI images associated with successive complete ACS data sets referred to in FIG. 5. Ten images associated with the even valued complete ACS data sets are shown rather than 19 images. FIG. 6 includes images reconstructed from ACS data sets during which subject motion is introduced. Image rows 603, 605, 607 and 609 correspond to four different acquisitions of ACS data sets during which varying amounts of motion are introduced for interleaved 2-shot EPI ACS segments. Image row 609 is acquired as the subject tried to remain motionless throughout ACS acquisition. For each of the acquisitions, the dashed lines enclose the GRAPPA reconstructed images for which $M_s$ is highest and the solid lines enclose the images for which $M_s$ is lowest. In each of the enclosed images the value of $M_s$ is given in the upper left corner.

System 10 (FIG. 2) advantageously uses navigator echoes, conveniently already part of a usual EPI scan, as a means of assessing motion corruption of GRAPPA ACS data. The system retrieves sufficiently motion-uncontaminated ACS data from a series of complete ACS datasets and enhances the robustness of GRAPPA-accelerated EPI for FMRI (functional MRI), where subject motion during an initial part of image acquisition, the interleaved ACS, can render an entire time series worthless. In one embodiment the system loops on the ACS acquisition until the metric $M_s$ meets a predetermined criterion, thereby assuring that an acceptable image is produced in the presence of protracted motion during ACS acquisition. Graphical plot 509 of FIG. 5 together with row 609 of FIG. 6 indicate a criterion is usable for the metric $M_s$. When using an embedded ACS method, the value of $M_s$ may be calculated for each complete embedded ACS set. The complete ACS data set which is both temporally nearest to the time series point of interest and which meets the criterion for the metric $M_s$ is used for auto-calibration at that point in the EPI time series.

In another embodiment the system detects if significant motion is in the phase-encoding direction and inserts another navigator to detect additional orthogonal motion. Thereby the system addresses potential directional dependence of the navigators since the navigators are projections along the phase-encoding axis for a 2D slice of image data. With increasing R, field strength or EPI echo-spacing time the effects of main field inhomogeneity on single-shot ACS data acquisition become increasingly pronounced, indicating a need for interleaved ACS data acquisition when using the non-embedded ACS data. The use of embedded ACS data can diminish artifacts due to motion between the time of ACS acquisition and the time of the reduced data set acquisition within the EPI time-series. The system simultaneously takes advantage of the inherent benefits of non-embedded or embedded segmented ACS data acquisition while avoiding the potential artifacts due to motion occurring between the acquisition of the ACS data segments which is of particular value in FMRI where motion can be a source of error in parallel imaging.

The system is usable in multiband sequences, where image acquisition acceleration (reducing acquisition time) is in the slice direction instead of conventional phase encoding direction and where coil sensitivity information is still required. The system is also usable in image acquisition acceleration in a slice direction using reference data acquired with separate sets of RF coils. The system is also usable with metrics other than those requiring navigator echoes to assess the motion between ACS segments. A metric assesses the degree of mismatch between the looped k-space segments, or assesses the extent and amplitude of residual aliasing in the image domain resulting from the possible combinations of ACS segments.

The system in one embodiment compensates for patient movement-related artifacts occurring in time series of echo planar images (EPI) acquired by using the GRAPPA (Generalized Autocalibrating Partially Parallel Acquisition) method of parallel magnetic resonance imaging (MRI). The system in one embodiment employs a main magnetic field generator for generating a magnetization density in a patient, a radio frequency generator to coherently reorient the magnetization density after which the magnetization precesses and generates an electromagnetic signal. The system uses a multi-channel array of receiver coils individually possessing focal spatial sensitivity for acquiring the signal, applied known inhomogeneous fields to provide spatial frequency (k-space) encoded data, at least one computer equipped to control the real-time functions and a computer for reconstructing images from the k-space data.

A system reconstruction computer (system computer 20, FIG. 2) is equipped with GRAPPA reconstruction functions to synthesize missing k-space phase-encoded data. This is done using a reduced set of acquired phase-encoded data with the sampling interval in the phase-encoding direction being RΔk where the union of the missing and reduced sets comprise a complete set of phase-encoded data with the sampling interval in the phase-encoding direction being Δk and with the ratio of the number of phase-encoded lines in the reduced set to the number of phase-encoded lines in the complete set being the reduction factor R. The GRAPPA reconstruction method calculates a set of synthesis coefficients taking a subset of the phase-encoded data of the complete set of data from each receiver channel, known as an auto-calibration signal (ACS) and being sampled at intervals in the phase-encoding direction of Δk, as input to the method and the synthesis coefficients comprise output of the method. The synthesis coefficients and the reduced data set for each channel are the input data to a method which outputs the complete data set for each channel of the receiver. The set of data for each channel is used to reconstruct an image for each channel by Fourier transform and the set of images for each channel are combined in one of a number of ways to generate a final image.

The system uses ACS data acquired in R EPI interleaves with the sampling interval in the phase-encoding direction being RΔk for each interleave and with each interleave of a complete set of ACS data, comprised of R interleaves, being acquired with an intervening interval of time but otherwise similar to the reduced data set except for a shift in the phase-encoding direction equal to Δk. The system uses multiple acquired complete sets of ACS data, acquired prior to a time series of reduced data sets or embedded within the time series of reduced data sets, and the phase correction data acquired along with each interleave as input to a method which chooses the best complete set of ACS data from the multiple acquired complete ACS data sets. In one embodiment, the best complete set of ACS data is established in response to a motion metric derived based on phase correction data for each interleave. The system uses the metric to establish which of the multiple acquired complete ACS data sets is least contaminated by motion and hence the best complete ACS data set. The metric associated with the best complete set of ACS data may in addition be required to be less than a predetermined threshold value. The best set of complete ACS data is used as input to a GRAPPA method which calculates the synthesis coefficients.

Figure 7:
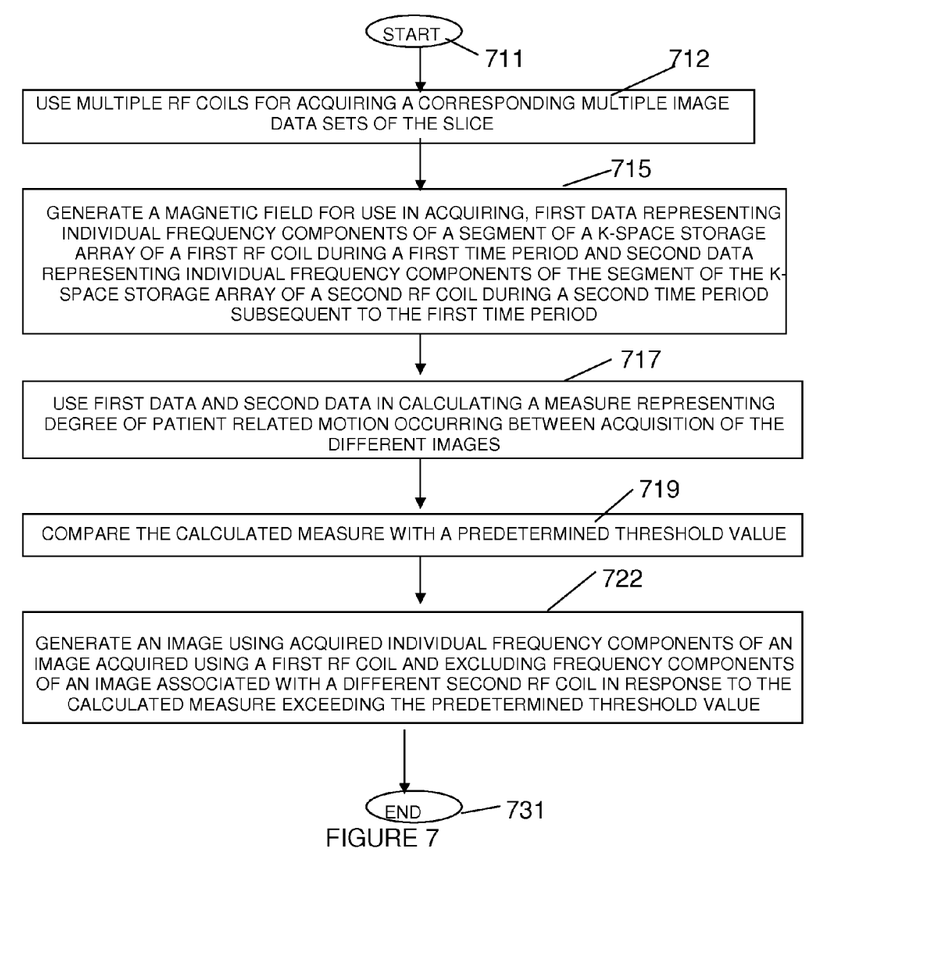
FIG. 7 shows a flowchart of a process performed by a system for compensating for patient movement related artifacts occurring in MR imaging, according to an embodiment of the invention.

FIG. 7 shows a flowchart of a process performed by system 10 (FIG. 2) for automatically compensating for patient movement related artifacts occurring in MR imaging according to an embodiment of the invention. In step 712 following the start at step 711 multiple MR imaging RF coils 4 (FIG. 2) of MR imaging system 10 individually receive MR imaging data representing a slice of patient anatomy and RF coils 4 acquire corresponding multiple image data sets of the slice. In step 715 RF coils 4 (a magnetic field generator) generate a magnetic field for use in acquiring, first data representing individual frequency components of a segment of a k-space storage array of a first RF coil during a first time period and second data representing individual frequency components of the segment of the k-space storage array of a second RF coil during a second time period subsequent to the first time period. The first data and the second data comprise individual frequency components of different images of a single image slice of a patient acquired using corresponding different RF coils in parallel imaging the image slice.

The first data and the second data represent individual frequency components (e.g. individual phase components) of auto calibration image data sets acquired during Echo Planar Imaging and the image data processor excludes auto calibration image data showing largest degree of motion as indicated by the calculated measure. The first data and the second data comprise individual frequency components of different images of a single image slice of a patient acquired using corresponding different RF coils in parallel imaging the image slice. The first data and the second data represent individual frequency components of a segment of a k-space comprising at least one of, (a) a line of k-space, (b) a central portion of k-space and (c) a peripheral portion of k-space. In another embodiment, the first data and second data represent images from different slices, and at least one of the first data and second data are used for reducing image acquisition time in a slice direction. Further, the first data and second data represent images from different RF coils.

An image data processor in system computer 20 in step 717, uses the first data and second data in calculating a measure representing degree of patient related motion occurring between acquisition of the different images. The measure is calculated in response to a difference in values of corresponding frequency components (which may have been Fourier Transformed in one embodiment, for example) of the first data and the second data. The measure is calculated in response to at least one of, (a) a square of the difference, (b) a mean square of the difference and (c) a root means square of the difference. In one embodiment, the measure is calculated using a function of the form, $$M_s = \sqrt{\frac{\sum_{m=1}^{N_c}\sum_{n=1}^{N_s}\sum_{j=1}^{R-1} \|S_{sjm}[n] - S_{s,j+1,m}[n]\|^2}{\sum_{m=1}^{N_c}\sum_{n=1}^{N_s} \|S_{s1m}[n]\|^2}}$$

where, $S_{sjm}[n]$ is the frequency-encoded signal (which comprises an FFT of the raw signal in one embodiment, for example), j is the ACS segment index, m is the coil element index and n is the signal sample index. The image data processor in step 719 compares the calculated measure with a predetermined threshold value.

In step 722, the image data processor generates an image using acquired individual frequency components of an image acquired using a first RF coil and excluding frequency components of an image associated with a different second RF coil in response to the calculated measure exceeding the predetermined threshold value. The image data processor generates the image using acquired individual frequency components of adjacent segments of the k-space storage array excluding frequency components of an image associated with an RF coil in response to the calculated measure exceeding the predetermined threshold value. The process of FIG. 7 terminates at step 731.

Returning to FIG. 2, in the basic field magnet 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times. Homogeneity of the base magnetic field B0 is corrected using shim coils 2 electrically powered by shim coil supply 15.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via a radio-frequency amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

Definitions. The following definitions are presented to assist with the understanding of the invention. These definitions are not intended to alter the ordinary meaning of the terms, but to provide a quick reference to terminology that would be understood by those skilled in the art by reading the disclosure herein.

EPI=Echo planar imaging involves image acquisition whereby a complete image is formed from a single data sample (k-space lines are acquired in one repetition time) of a gradient echo or spin echo sequence.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI=inversion time, the time between an inversion recovery pulse and the next RF excitation pulse. TI determines the image contrast.

$T_1$=the longitudinal (or spin-lattice) relaxation time $T_1$ decay constant.

$T_2$=the transverse (or spin-spin) relaxation time $T_2$ is the decay constant for a proton spin component.

TR=repetition time, the time between successive RF excitation pulses.

B0 is the main static base MRI magnetic field.

B1 is the RF transmit coil field.

The system and processes of FIGS. 2-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An MR parallel imaging system compensates for patient movement related artifacts occurring in MR imaging using an auto-calibration scan (ACS) by excluding use of auto-calibration image data in response to a calculated measure representing motion between ACS image data elements exceeding a predetermined threshold value. Further, the processes and applications may, in alternative embodiments, be located on one or more (e.g., distributed) processing devices on a network linking the units of FIG. 2. Any of the functions and steps provided in FIGS. 2-7 may be implemented in hardware, software or a combination of both.

From the discussion above it will be appreciated that the invention can be embodied in various ways, including the following:

1. A system for compensating for patient movement related artifacts occurring in MR imaging, the system comprising: (a) a magnetic field generator for generating a magnetic field for use in acquiring (i) first data representing individual frequency components of a segment of a k-space storage array during a first time period and (ii) second data representing individual frequency components of the segment of the k-space storage array during a second time period subsequent to the first time period, the first data and the second data comprising individual frequency components of different images of a portion of the anatomy of a patient; and (b) an image data processor for (i) using the first data and second data in calculating a measure representing degree of patient related motion occurring between acquisition of the first data and second data, (ii) comparing the calculated measure with a predetermined threshold value and (iii) generating an image using acquired individual frequency components of adjacent segments of the k-space storage array excluding frequency components of the first data and second data in response to the calculated measure exceeding the predetermined threshold value.

2. The system of embodiment 1, wherein the measure is calculated in response to a difference in Fourier Transform values of corresponding frequency components of the first data and the second data.

3. The system of embodiment 2, wherein the measure is calculated in response to at least one of, (a) a square of the difference, (b) a mean square of the difference and (c) a root means square of the difference.

4. The system of embodiment 3, wherein the measure is calculated using a function of the form, $$M_s = \sqrt{\frac{\sum_{m=1}^{N_c} \sum_{n=1}^{N_s} \sum_{j=1}^{R-1} \|S_{sjm}[n] - S_{s,j+1,m}[n]\|^2}{\sum_{m=1}^{N_c} \sum_{n=1}^{N_s} \|S_{s1m}[n]\|^2}}$$

where, $S_{sjm}[n]$ is the frequency-encoded signal, j is the ACS segment index, m is the coil element index and n is the signal sample index.

5. The system of embodiment 1, wherein the first data and the second data represent individual frequency components of a segment of a k-space comprising at least one of, (a) a line of k-space, (b) a central portion of k-space and (c) a peripheral portion of k-space.

6. The system of embodiment 1, wherein the first data and the second data represent individual frequency components of auto calibration image data sets acquired during Echo Planar Imaging.

7. The system of embodiment 1, wherein the first data and the second data comprise individual frequency components of different images of a portion of the anatomy of a patient acquired using corresponding different RF coils in parallel imaging the portion of the anatomy.

8. The system of embodiment 7, wherein the image data processor: (a) uses the first data and second data in calculating a measure representing degree of patient related motion occurring between acquisition of the different images, and (b) generates an image using acquired individual frequency components of adjacent segments of the k-space storage array excluding frequency components of an image associated with an RF coil in response to the calculated measure exceeding the predetermined threshold value.

9. The system of embodiment 1, wherein the individual frequency components comprise individual phase components.

10. The system of embodiment 1, wherein the first data and the second data represent auto calibration image data sets acquired during Echo Planar Imaging and the image data processor excludes auto calibration image data showing largest degree of motion as indicated by the calculated measure.

11. The system of embodiment 1, wherein the first data and second data represent images from different slices, and at least one of the first data and second data are used for reducing image acquisition time in a slice direction.

12. The system of embodiment 1, wherein the first data and second data represent images from different RF coils.

13. A system for compensating for patient movement related artifacts occurring in parallel image processing in MR imaging, comprising: (a) a plurality of MR imaging RF coils for individually receiving MR imaging data representing a slice of patient anatomy; (b) an MR imaging system for using the plurality of RF coils for acquiring a corresponding plurality of image data sets of the slice; (c) a magnetic field generator for generating a magnetic field for use in acquiring (i) first data representing individual frequency components of a segment of a k-space storage array of a first RF coil during a first time period, and (ii) second data representing individual frequency components of the segment of the k-space storage array of a second RF coil during a second time period subsequent to the first time period, (iii) the first data and the second data comprising individual frequency components of different images of a portion of the anatomy of a patient acquired using corresponding different RF coils in parallel imaging the image slice; and (d) an image data processor for (i) using first data and second data in calculating a measure representing degree of patient related motion occurring between acquisition of the different images, (ii) comparing the calculated measure with a predetermined threshold value, and (ii) generating an image using acquired individual frequency components of an image acquired using a first RF coil and excluding frequency components of an image associated with a different second RF coil in response to the calculated measure exceeding the predetermined threshold value.

14. A system for compensating for patient movement related artifacts occurring in MR imaging, comprising: (a) a magnetic field generator for generating a magnetic field for use in acquiring (i) first data representing individual frequency components of a k-space storage array comprising first calibration image data during a first time period, and (ii) second data representing individual frequency components of the k-space storage array comprising second calibration image data during a second time period subsequent to the first time period, the first data and the second data comprising individual frequency components of different calibration images of a portion of the anatomy of a patient; and (b) an image data processor for (i) using the first data and second data in calculating a measure representing degree of patient related motion occurring between acquisition of the first data and second data, (ii) comparing the calculated measure with a predetermined threshold value, and (iii) excluding using calibration image data in response to the calculated measure exceeding the predetermined threshold value.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s). Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A system for compensating for patient movement related artifacts occurring in MR imaging, comprising:
   (a) a magnetic field generator for generating a magnetic field for use in acquiring,
      (i) first data representing individual frequency components of a segment of a k-space storage array during a first time period, and
      (ii) second data representing individual frequency components of the segment of the k-space storage array during a second time period subsequent to said first time period, said first data and said second data comprising individual frequency components of different images of a portion of the anatomy of a patient; and
   (b) an image data processor for,
      (i) using the first data and second data in calculating a measure representing degree of patient related motion occurring between acquisition of the first data and second data,
      (ii) comparing the calculated measure with a predetermined threshold value, and
      (iii) generating an image using acquired individual frequency components of adjacent segments of the k-space storage array excluding frequency components of the first data and second data in response to said calculated measure exceeding said predetermined threshold value.

2. A system according to claim 1, wherein said measure is calculated in response to a difference in Fourier Transform values of corresponding frequency components of said first data and said second data.

3. A system according to claim 2, wherein said measure is calculated in response to at least one of, (a) a square of said difference, (b) a mean square of said difference and (c) a root means square of said difference.

4. A system according to claim 3, wherein said measure is calculated using a function of the form, $$M_s = \sqrt{\frac{\sum_{m=1}^{N_c} \sum_{n=1}^{N_s} \sum_{j=1}^{R-1} \|S_{sjm}[n] - S_{s,j+1,m}[n]\|^2}{\sum_{m=1}^{N_c} \sum_{n=1}^{N_s} \|S_{s1m}[n]\|^2}}$$

where, $S_{sjm}[n]$ is the frequency-encoded signal, j is the ACS segment index, m is the coil element index and n is the signal sample index.

5. A system according to claim 1, wherein said first data and said second data represent individual frequency components of a segment of a k-space comprising at least one of, (a) a line of k-space, (b) a central portion of k-space and (c) a peripheral portion of k-space.

6. A system according to claim 1, wherein said first data and said second data represent individual frequency components of auto calibration image data sets acquired during Echo Planar Imaging.

7. A system according to claim 1, wherein said first data and said second data comprise individual frequency components of different images of a portion of the anatomy of a patient acquired using corresponding different RF coils in parallel imaging said portion of the anatomy.

8. A system according to claim 7, wherein said image data processor,
   uses the first data and second data in calculating a measure representing degree of patient related motion occurring between acquisition of the different images, and
   generates an image using acquired individual frequency components of adjacent segments of the k-space storage array excluding frequency components of an image associated with an RF coil in response to said calculated measure exceeding said predetermined threshold value.

9. A system according to claim 1, wherein said individual frequency components comprise individual phase components.

10. A system according to claim 1, wherein said first data and said second data represent auto calibration image data sets acquired during Echo Planar Imaging and said image data processor excludes auto calibration image data showing largest degree of motion as indicated by said calculated measure.

11. A system according to claim 1, wherein the first data and second data represent images from different slices, and at least one of said first data and second data are used for reducing image acquisition time in a slice direction.

12. A system according to claim 1, wherein the first data and second data represent images from different RF coils.

13. A system for compensating for patient movement related artifacts occurring in parallel image processing in MR imaging, comprising:
   (a) a plurality of MR imaging RF coils for individually receiving MR imaging data representing a slice of patient anatomy;

(b) an MR imaging system for using the plurality of RF coils for acquiring a corresponding plurality of image data sets of said slice;
(c) a magnetic field generator for generating a magnetic field for use in acquiring,
  (i) first data representing individual frequency components of a segment of a k-space storage array of a first RF coil during a first time period, and
  (ii) second data representing individual frequency components of the segment of the k-space storage array of a second RF coil during a second time period subsequent to said first time period, said first data and said second data comprising individual frequency components of different images of a portion of the anatomy of a patient acquired using corresponding different RF coils in parallel imaging said image slice; and
(d) an image data processor for,
  (i) using first data and second data in calculating a measure representing degree of patient related motion occurring between acquisition of the different images,
  (ii) comparing the calculated measure with a predetermined threshold value, and
  (iii) generating an image using acquired individual frequency components of adjacent segments of the k-space storage array excluding frequency components of the first data and the second data in response to said calculated measure exceeding said predetermined threshold value.

14. A system for compensating for patient movement related artifacts occurring in MR imaging, comprising:
(a) a magnetic field generator for generating a magnetic field for use in acquiring,
  (i) first data representing individual frequency components of a k-space storage array comprising first calibration image data during a first time period, and
  (ii) second data representing individual frequency components of the k-space storage array comprising second calibration image data during a second time period subsequent to said first time period, said first data and said second data comprising individual frequency components of different calibration images of a portion of the anatomy of a patient;
(b) an image data processor for,
  using the first data and second data in calculating a measure representing degree of patient related motion occurring between acquisition of the first data and second data,
  (ii) comparing the calculated measure with a predetermined threshold value, and
  (iii) generating an image using acquired individual frequency components of adjacent segments of the k-space storage array excluding frequency components of the first data and the second data in response to said calculated measure exceeding said predetermined threshold value.

* * * * *

UNITED STATES PATENT AND TRADEMARK OFFICE
CERTIFICATE OF CORRECTION

PATENT NO. : 8,934,691 B2  
APPLICATION NO. : 13/412766  
DATED : January 13, 2015  
INVENTOR(S) : Daniel James Sheltraw, Vibhas S. Deshpande and Benjamin Alastair Inglis Page 1 of 1

It is certified that error appears in the above-identified patent and that said Letters Patent is hereby corrected as shown below:

On the Title Page

In item (75) Inventors: --Vibhas S. Despande should read Vibhas S. Deshpande--

Signed and Sealed this  
Tenth Day of February, 2026

John A. Squires  
*Director of the United States Patent and Trademark Office*